United States Patent [19]

Fujimura et al.

[11] Patent Number: 5,166,068

[45] Date of Patent: Nov. 24, 1992

[54] METHOD OF CULTURING PROTOPLASTS

[75] Inventors: Tatsuhito Fujimura, Tokyo; Motoi Sakurai, Ashigarakami, both of Japan

[73] Assignee: Mitsui Toatsu Chemicals, Inc., Tokyo, Japan

[21] Appl. No.: 865,422

[22] Filed: May 21, 1986

[30] Foreign Application Priority Data

May 21, 1985 [JP] Japan ................... 60-106885

[51] Int. Cl.$^5$ .................... C12N 5/02; C12N 5/00
[52] U.S. Cl. .................... 435/240.47; 435/240.54
[58] Field of Search ............ 47/58; 435/240.49, 240.5, 435/240.54, 172.2, 240.47, 240.45, 240.4

[56] References Cited

U.S. PATENT DOCUMENTS 4,880,744 11/1989 Fujimura et al. .............. 435/240.46

FOREIGN PATENT DOCUMENTS 0202667 11/1986 European Pat. Off. .
0202669 11/1986 European Pat. Off. .
0134536 10/1987 European Pat. Off. .

OTHER PUBLICATIONS

Aviv et al. (1984) in Cell Culture & Somatic Cell Genetics of Plants, vol. 1.
Nomura et al. (1983) Plant Science Letters 29, 1-7.
Wakasa et al (1984) J Plant Physical 117: 223-31.
Gamborg et al. (1981) in T. A. Thorpe, ed., *Plant Tissue Culture*, Academic Press, N.Y., pp. 115-117, 120-124.
Gamborg (1984) in IK Vasil, ed., Cell Culture and Somatic Cell Genetics of Plants, vol. 1, Academic Press, N.Y., pp. 18-26.
Flores et al. (1981) in Advances in Cell Culture, vol. 1, K. Maramorssch, ed., Academic Press, N.Y., pp. 247-248.
Vasil et al, "Cell Culture and Somatic Cell Genetics of Plants" vol. 1, Chapter 45, pp. 398-404 (1984).
Vasil et al, "Colloq. Intern. Centre. Natl. Rech. Sci.", vol. 212, pp. 139-149 (1972).
Deka et al, "Molec. gen. Genet.", 145, pp. 239-243 (1976).
Cai et al, "Biological Abstracts", vol. 68, Abstract No. 11595 (1979).
Fujimura et al, "Plant Tissue Culture Letters", 2 (2), pp. 74-74 (1985).
Potrykus et al, "Theor. Appl. Genet.", 54, pp. 209-214 (1979).
Fraley et al, "Proc. Natl. Acad. Sci. USA", vol. 80, No. 15, pp. 4803-4807 (1983).
Herrera-Estrella et al, "The EMBO Journal", vol. 2, No. 6, pp. 987-995 (1983).
Hess et al, "Chemical Abstracts", 83:5347s, p. 471 (1975).
Ohno et al, Japanese Journal of Breeding 35, pp. 54-55 (1985).
Nishi et al, Nature 219, pp. 508-509 (1968).

*Primary Examiner*—David T. Fox
*Attorney, Agent, or Firm*—Birch, Stewart, Kolasch & Birch

[57] ABSTRACT

Disclosed is a method of culturing protoplasts in a liquid medium. According to the method, the protoplasts are cultured in a liquid medium layer having a thickness of about 100 to about 400 $\mu$m.

20 Claims, No Drawings of a plant.

METHOD OF CULTURING PROTOPLASTS

BACKGROUND OF THE INVENTION

1. Field of the Invention

This invention relates to a method of culturing a protoplast. More specifically, this invention relates to a method of culturing a protoplast in a liquid medium, by which a callus or a cell cluster is derived from the protoplast.

2. Description of the Prior Art

Protoplast is a cell of a plant, bacterium, fungus and the like from which the cell wall has been removed. Since the protoplast does not have a cell wall, it is easily subjected to an artificial manipulation such as cell fusion, gene manipulation and artificial somatic cell mutation. Thus, if a complete plant can be regenerated from a protoplast manipulated, it would be possible to obtain a plant which has an advantageous characteristic which the wild type plant does not have. It is known for many plants that a complete plant can be regenerated from a callus or a cell cluster. Thus, if a callus can be derived from a protoplast, a complete plant is likely to be regenerated from the callus, and in turn, from the protoplast.

Some techniques are known for dicotyledons such as tobacco by which a complete plant can be regenerated from a protoplast. However, as for the gramineous plants such as rice, wheat and corn, complete plants were reported to be regenerated only for corn and pasture. As to rice, very few techniques have been reported as mentioned below. The conventional culturing methods of the protoplasts include culturing the protoplasts by embedding the protoplast in a semi-solid agar medium, by suspending the protoplast in a liquid medium, and by culturing the protoplast using feeder cells. However, it has been found that these techniques are often not effective for culturing other plants such as gramineous plants including rice, wheat and corn. For example, if a protoplast of rice is cultured by one of these methods, the protoplast dies or cannot grow.

As for culturing techniques of the protoplast of rice, it has been reported that a callus was derived from a protoplast obtained from a cell lacking its nitrate reductase (Wakasa et al., J. Plant Physiol. 117: pp.223-231, (1984)), and a shoot was generated from a callus derived from a protoplast obtained from a callus of a pollen (Ohno et al., Japanese Journal of Breeding 35: pp.54-55, (1985)). However, these techniques utilize protoplasts released from specific calli, and the techniques are applicable to not all kinds of protoplasts released from various kinds of calli or tissues. In other words, these techniques are not reproducible for most kinds of protoplasts.

On the other hand, it has been reported by many researchers that complete plants were regenerated from cultured cells of rice (Nishi et al., Nature 219: pp.508-509, (1968)). However, these techniques do not utilize the protoplast. Further, it has been found that obtaining a protoplast from the cells having a high differentiation ability used in these techniques is difficult, and to culture the protoplast is also difficult.

Thus, a method of culturing protoplasts is needed to be established by which a callus or a cell cluster derived from the protoplast, which method is reproducible and applicable to protoplasts orginated from a general or a non-specific cell of a plant.

SUMMARY OF THE INVENTION

Accordingly, an object of the present invention is to provide a method of culturing a protoplast by which a cell cluster or a callus is derived from the protoplast, which method is reproducible and applicable to those protoplasts originated from a general or a non-specific cell of a plant.

In the method of the present invention, the protoplasts are cultured in a layer of liquid medium of of 100 to 400 $\mu$m thickness. By the method of the present invention, the protoplasts are cultured in a somewhat aerobic condition. It has been found by the present inventors that this aerobic condition promotes the growth of the protoplasts.

By the method of the present invention, not only the protoplasts of dicotyledons, but also even the protoplasts of monocotyledons can be grown well to form calli or cell clusters.

DETAILED DESCRIPTION OF THE PREFERRED EMBODIMENTS

As mentioned above, according to the method of the present invention, the protoplasts are cultured in a layer of a liquid medium of which thickness is about 100 to about 400 $\mu$m, and preferably 200 to 300 $\mu$m. According to the method of the present invention, the protoplasts are cultured in a somewhat aerobic condition, and this aerobic condition is believed to promote the growth of the protoplasts. If the thickness of the liquid medium is more than about 400 $\mu$m, the oxygen supply to the protoplasts becomes insufficient, and if it is less than about 100 $\mu$m, the protoplasts may be adversely affected by the liquid-air interface.

It may be difficult to form such a thin layer of a liquid medium because of the surface tension of the liquid. That is, if a small amount of liquid medium is placed on a plastic Petri dish or the like, the liquid medium forms spherical water drops or beads due to its surface tension. Making such a thin layer of a liquid medium was accomplished by the present inventors by placing the liquid medium on a hydrophilic support, thereby reducing the surface tension of the liquid medium. Preferred hydrophilic supports include agar, alginic acid and salts thereof, and gelatin. Thus, the thin layer of the liquid medium can be formed by placing the liquid medium in a Petri dish of which bottom surface is coated with a hydrophilic support. Since the hydrophilic supports absorb the culture medium as well as the protoplasts, it is preferred that the thickness of the hydrophilic support be as thin as possible. Thus, the preferred thickness of the hydrophilic support is not more than 1 mm, and more preferably, not more than 200 $\mu$m. It is also preferred that the hydrophilic support contain an osmoticum such as sucrose, mannitol and glucose. Further, the hydrophilic support may contain phytohormones, vitamins and other nutrients which may be added to the liquid medium as mentioned below.

Any medium conventionally used for culturing protoplasts may be used in the method of the present invention. For example, if the protoplast to be cultured is a protoplast of rice (plants belonging to genus Oryza such as Oryza sativa, Oryza glaberrima and Oryza perennis and so on), MS medium (Murashige and Skoog, Physiol. Plant. 15, pp.473-479, (1962)), B5 medium (Gamborg et al., Exp. Cell Res. 50, pp.151-158, (1968)), N6 medium (Chu et al., Scientia Scinica 18, pp.659-663, (1975)) and R2 medium (Ohira et al., Plant Cell Physiol., 14, pp.1113–1121, (1973)) may be used as the culture medium. Similarly, if the protoplast to be cultured is a protoplast of petunia, NT medium (Nagata and Takebe, Planta 99, pp.12–20, (1971)) may be used. The medium may contain phytohormones such as 2,4-dichlorophenoxy acetic acid (hereinafter referred to as 2,4-D), benzyladenine, kinetin, zeatin, gibberellin, and absisic acid; vitamins such as nicotinic acid, thiamine and pyridoxine; sugars and sugar alcohols such as sucrose and mannitol; and other nutrients, which are conventionally added to the culture media for culturing protoplasts. The concentration of these additives may be suitably selected depending on the nature of the protoplast to be cultured and on the nature of the additive, and may be, for example, 0.1 to 10 mg/l. It has also been found by the present inventors that if the medium contains a used medium in which a plant cell or a protoplast was cultured before, the growth of the protoplasts is further promoted. Further, it is preferred to adjust the pH of the medium to not more than 5.2, and preferably 3.5 to 5.2.

The culturing conditions per se may be conventional. Thus, the culturing conditions may be appropriately selected depending on the nature of the protoplast to be cultured. For example, if the protoplast to be cultured is a protoplast of rice, the culturing temperature may be 20° to 30° C., and preferably about 26°0 C., and the cell concentration of the protoplasts in the liquid medium may be $10^4$ to $10^7$/ml and preferably $10^5$ to $5 \times 10^6$/ml.

The method of the present invention may be applied to the culture of protoplasts prepared by any method. A number of methods to release protoplasts are known for various kinds of plants. If the protoplast to be cultured is a protoplast of rice, the protoplast may be, for example, obtained from a callus of rice by treating the callus with an enzymatic solution containing 0.1 to 10% by weight, preferably 1 to 5% by weight of cellulase, 0.1 to 5% by weight, preferably 0.5 to 2% by weight of a macerating enzyme, 0 to 5% by weight, preferably 0.1 to 1% by weight of calcium chloride, and 0 to 5% by weight, preferably 0.1 to 1% by weight of potassium salt of dextran sulfate.

This invention will be more readily understood by referring to the following examples. It should be noted that the following examples are presented for the illustration purpose only, and the scope of the invention is by no means limited thereto.

EXAMPLE 1

Culture of Protoplasts of Rice Preparation of Protoplasts

Seeds of rice (Oryza sativa cultivar, variety: Nihonbare) were immersed in 70% aqueous solution of ethanol for one minute, and then immersed in an aqueous solution of sodium hypochlorite (chlorine content of 5% by weight) for 15 minutes. The seeds were then washed with sterilized distilled water three times and then sowed on N6 agar medium containing 0.3% by weight of casein hydrolysate, 2ppm of 2,4-D and 1 ppm of benzyladenine. After culturing at 26° C. for three weeks, calli were formed from the scutella of the seeds. These calli were subcultured once every four weeks in the same conditions.

The thus obtained calli were suspended in R2 liquid medium containing 0.3% by weight of casein hydrolysate and 1 ppm of 2,4-D. The cells were subcultured once a week. The cell clusters obtained at 5 to 7 days after subculture were used for preparing protoplasts in the next step.

The thus obtained cell clusters were treated with a solution containing 4.0% by weight of Cellulase Onozuka RS (commercially available from Yakult Pharmaceutical), 1.0% by weight of Macerozyme R-10 (commercially available from Yakult Pharmaceutical), 0.5% by weight of calcium chloride, 0.5% by weight of potassium salt of dextran sulfate, and 0.4M of mannitol as an osmoticum. The cells were then gently shaken in this solution for 6 hours at 27° C. to obtain protoplasts. Then the enzymatic solution containing the protoplasts was filtered to remove the undigested cell clusters, and the filtrate was centrifuged at 50 g for 5 minutes to precipitate the protoplasts. The precipitated protoplasts were washed three times with 0.4M aqueous solution of glucose and were cultured in the next step.

Coating of the Bottom Surface of the Container with a Hydrophilic Support

Plastic Petri dishes of 35 mm diameter were used as the containers of the culture media. The bottom surface of each of the Petri dishes was coated with about 100 μl of 0.8% agar (manufactured by Difco) containing R2 medium as its basal medium, vitamines of B5 medium, and 0.4M sucrose to form an agar layer of about 100 μm thickness.

Formulation of the Culture Medium for Culturing Protoplasts of Rice

Calli derived from the immature embryos of seeds of rice (Oryza sativa cultivar, variety: Sasanishiki) were cultured in R2 liquid medium containing 0.3% by weight of casein hydrolysate and 1 ppm of 2,4-D. This culture was continuously subcultured for once a week by adding 10 ml of the culture to 20 ml of fresh medium of the same composition.

A subculture at 4 to 7 days after subculturing was filtered to remove the cells. To 10 ml of the thus obtained filtrate, were added 50 μl of 100 ppm 2,4-D, 1.37 g of sugar and trace amount of vitamins. The pH of this filtrate was adjusted to 4.5 with 0.1 N HCl. This medium was then filtered through a membrane filter to sterilize the same, and was used as the medium for culturing protoplasts in the next step.

To each of the Petri dishes of which bottom surface was coated with agar as described above, 40 to 400 μl of the medium obtained as mentioned above containing $10^6$ protoplasts/ml was added and was uniformly spread, thereby forming a layer of the liquid medium of 50 to 500 μm thickness. After sealing the Petri dishes, culture was conducted in the dark at 26° C. for 30 days. The formation of cell clusters was observed using an inverted microscope. The results are shown in Table 1.

TABLE 1

| Formation of Cell Clusters | |
|---|---|
| Thickness of Liquid Medium | Formation of Cell Clusters |
| 50 μm | − |
| 100 μm | + |
| 200 μm | ++ |
| 300 μm | ++ |
| 400 μm | + |
| 500 μm | − |

−: No cell clusters were formed
+: Several cell clusters were formed
++: Several hundreds of cell clusters were formed As shown in Table 1, formation of cell clusters was observed when the thickness of the liquid medium was 100 to 400 μm, and especially good results were obtained by using liquid medium of 200 to 300 μm thickness.

EXAMPLE 2

Culture of Protoplasts of Carrot

Calli derived from hypocotyls of carrots cultured in a liquid medium containing 0.1 ppm of 2,4-D were treated with a solution containing 2% by weight of Cellulase Onozuka R-10, 1% by weight of Macerozyme R-10, 2% by weight of Driselase (commercially available from Kyowa Hakko), 0.5% by weight of calcium chloride and 0.7M of mannitol. After gently shaking the mixture for 3 hours at 26° C. to release protoplasts, the mixture was filtered through a 300 mesh Nylon sieve to remove undigested cell clusters The filtrate was centrifuged at 100 g for 5 minutes to precipitate the protoplasts. The precipitated protoplasts were washed three times with 0.5M mannitol.

The thus obtained protoplasts were suspended in MS liquid medium containing 1 ppm of 2,4-D and 0.5M mannitol at a cell concentration of $10^5$/ml. A plastic Petri dish of 35 mm diameter was coated with a 0.8% agar containing the components of MS medium and 0.5M mannitol in the same manner as in Example 1. To this Petri dish, 300 μl of the above suspension was added and uniformly spread. Culture was conducted in the dark at 26° C. for 20 days. The number of the formed cell clusters was counted. As a control, the above suspension was added to the same Petri dish but not coated with the agar, and the protoplasts were cultured in the same manner. In this case, the suspension was not spread uniformly but became small drops due to its surface tension. The number of formed cell clusters was counted. The results are shown in Table 2.

TABLE 2

| Formation of Small Cell Clusters of Carrot | |
|---|---|
| Coating | Formation of Cell Clusters |
| Without Coating | + |
| With Coating | ++ |

+: Several tens of cell clusters were formed
++: Several hundreds of cell clusters were formed As shown in Table 2, by spreading the cell suspension uniformly on the agar coating, many more cell clusters were formed than those formed by adding the cell suspension to a non-coated Petri dish in which the suspension became small drops or beads.

EXAMPLE 3

Culture of Protoplasts of Petunia

A mature leaf of petunia grown in a greenhouse was immersed in 70% aqueous solution of ethanol for 10 seconds. The leaf was then immersed in an aqueous solution of 0.5% sodium hypochlorite (chlorine content of 0.5% by weight) for 10 minutes to sterilize it. After washing the leaf three times with sterilized distilled water, the leaf was shredded into pieces of 1 mm width. To a solution containing 1% by weight of Cellulase Onozuka R-10, 0.3% by weight of Macerozyme R-10 and 0.4M of mannitol, 0.5 g of the thus obtained shredded pieces were added, and the mixture was gently shaken for 5 hours at 26° C. to release protoplasts. The mixture was then filtered through a 250 mesh Nylon sieve to remove undigested cell clusters. The filtrate was centrifuged at 100 g for 5 minutes to precipitate the protoplasts. The precipitated protoplasts were washed three times with 0.4M mannitol.

The thus obtained protoplasts were suspended in NT medium containing 1 ppm of 2,4-D, 0.4ppm of benzyladenine, 50 mM of sugar and 0.3M of mannitol at a cell concentration of $10^5$/ml A plastic Petri dish of 35 mm diameter was coated with a 0.8% agar containing the components of NT medium in the same manner as in Example 1. To this Petri dish, 300 μl of the above suspension was added and uniformly spread. Culture was conducted in the dark at 26° C. for 20 days. The number of the formed cell clusters was counted. As a control, the above suspension was added to the same Petri dish but not coated with the agar, and the protoplasts were cultured in the same manner. In this case, the suspension was not spread uniformly but became small drops or beads due to its surface tension. The number of formed cell clusters was counted. The results are shown in Table 3.

TABLE 3

| Formation of Small Cell Clusters of Petunia | |
|---|---|
| Coating | Formation of Cell Clusters |
| Without Coating | + |
| With Coating | ++ |

+: Several tens of cell clusters were formed
++: Several hundreds of cell clusters were formed As shown in Table 3, by spreading the cell suspension uniformly on the agar coating, many more cell clusters were formed than by adding the cell suspension to a non-coated Petri dish in which the suspension became small drops.

We claim:

1. A method of culturing protoplasts, comprising: plating protoplasts of rice, carrot or petunia at a cell density sufficient to allow growth of said protoplasts in a liquid medium layer on a hydrophilic support which absorbs said liquid medium and which is capable of reducing the surface tension of said liquid medium layer, wherein the thickness of said liquid medium layer is about 100 to about 400 μm; and culturing said protoplasts in said liquid medium layer under aerobic conditions.

2. The method of claim 1 wherein the thickness of the liquid medium layer is about 200 to about 300 μm.

3. The method of claim 1 wherein the hydrophilic support is one selected from the group consisting of agar, alginic acid and salts thereof, and gelatin.

4. The method of claim 3 wherein the thickness of the hydrophilic support is not more than 1 mm.

5. The method of claim 4 wherein the thickness of the hydrophilic support is not more than 200 μm.

6. The method of claim 1 wherein the protoplast is a protoplast of rice.

7. The method of claim 6 wherein the rice is Oryza sativa.

8. The method of claim 6 wherein the medium comprises as its basal medium R2, N6, MS or B5 medium.

9. The method of claim 7 wherein the medium further comprises 0.1 to 10 mg/l of 2,4-D.

10. The method of claim 1, wherein said liquid medium layer is disposed on a thin flat hydrophilic layer which is coated on the surface of a cell culturing container.

11. The method of claim 10, wherein said cell culturing container is a Petri dish.

12. The method of claim 1, wherein said hydrophilic support contains an osmoticum.

13. The method of claim 1, wherein the cell concentration of protoplasts in the liquid medium is $10^4$ to $10^7$/ml and cultivation is carried out at a temperature of 20° to 30° C.

14. The method of claim 1, wherein cultivation is carried out for 20 days.

15. The method of claim 10, wherein said container is sealed during culturing.

16. A method of culturing proptoplasts, comprising: uniformly spreading a liquid culture medium containing protoplasts of rice, carrot or petunia at a cell density sufficient to allow growth of said protoplasts on a hydrophilic layer which absorbs said liquid culture medium to form a liquid culture medium layer having a thickness of about 100 to about 400 $\mu$m which is disposed on said hydrophilic layer; and culturing said protoplasts in said liquid culture medium layer under aerobic conditions while maintaining the thickness of said liquid culture medium layer at about 100 to about 400 $\mu$m.

17. The method of claim 16, wherein the thickness of said hydrophilic support layer is not more than 1 mm.

18. A method of culturing protoplasts, comprising:
uniformly spreading a liquid culture medium containing protoplasts of rice, carrot or petunia at a cell density sufficient to allow growth of said protoplasts to form a liquid culture medium layer having a thickness of about 100 to about 400 $\mu$m on a hydrophilic support layer which absorbs said liquid culture medium and which has a thickness of not more than 1 mm and which is capable of reducing the surface tension of said culture medium layer; and
culturing said protoplasts in contact with said liquid culture medium layer under aerobic conditions.

19. The method of claim 18, wherein said hydrophilic support is one selected from the group consisting of agar, alginic acid and salts thereof and gelatin.

20. The method of claim 18, wherein the thickness of said hydrophilic support layer is about 100 $\mu$m.

* * * * *